United States Patent [19]

Thorsgard

[11] Patent Number: 4,682,592
[45] Date of Patent: Jul. 28, 1987

[54] METHOD AND DEVICE FOR ACHIEVING REVERSIBLE MALE STERILIZATION

[76] Inventor: Knute E. Thorsgard, 3415 20th Ave. South, Apt. #210, Grand Forks, N. Dak. 58201

[21] Appl. No.: 695,188

[22] Filed: Jan. 28, 1985

[51] Int. Cl.[4] .............................................. A61B 19/00
[52] U.S. Cl. ................................. 128/303 R; 128/1 R
[58] Field of Search ................... 128/1 R, 303 R, 325, 128/341, 343

[56] References Cited

U.S. PATENT DOCUMENTS

| 3,589,355 | 6/1971 | Lee | 128/1 R |
|---|---|---|---|
| 3,687,129 | 8/1972 | Nuwayser | 128/1 R |
| 3,699,957 | 10/1972 | Robinson | 128/1 R |
| 3,750,194 | 8/1973 | Summers | 128/1 R X |
| 3,990,434 | 11/1976 | Free | 128/1 R |
| 4,013,063 | 3/1977 | Bucalo | 128/1 R |
| 4,142,516 | 3/1979 | Adair | 128/1 R |
| 4,244,370 | 1/1981 | Furlow et al. | 128/303 R |
| 4,271,835 | 6/1981 | Conn et al. | 604/15 |
| 4,503,569 | 3/1985 | Dotter | 128/303 R X |
| 4,512,342 | 4/1985 | Zaneveld et al. | 128/1 R X |

Primary Examiner—Kyle L. Howell
Assistant Examiner—Angela D. Sykes
Attorney, Agent, or Firm—Roberts & Floyd

[57] ABSTRACT

A male contraceptive which is effective, reversible and non-surgically implanted, which prevents the transport of sperm by occluding the lumen of the vas deferens, the ejaculatory duct, or the urethra. The male contraceptive is inserted and removed through the urethra. The contraceptive comprises an elongated hollow tube having an expandable elastic cap forming a fluid tight seal at one end and a plug forming a fluid tight seal at the other end. A flexible spring is provided within the tube. The plug includes a valve for allowing the selective ingress and egress of the fluid.

1 Claim, 3 Drawing Figures

METHOD AND DEVICE FOR ACHIEVING REVERSIBLE MALE STERILIZATION

CROSS-REFERENCE TO RELATED APPLICATION

This invention is not disclosed in any co-pending application for the patent or any issued patent.

BACKGROUND OF THE INVENTION

For centuries man has been concerned whether human population will exceed the food supply. This concern is particularly acute in certain countries where the percentage of the world population in that country is as high as three times the percentage of arable land in that country.

In recent years, man has become aware that he is rapidly depleting nonrenewable natural resources and is consuming renewable resources at a far greater rate than he is replacing them. This depletion is due in large part to the current unparallelled increase in the world's population, and will affect the future of the developed countries as well as the lesser developed countries.

For these and other reasons, many countries promote and encourage birth control. Indeed, some countries proscribe and sanction the multiple dependent family. In most of the world, various forms of birth control are available to men or women desiring to utilize them.

Historically, people have controlled contraception by relying on male methods of contraception. The condom was developed in the fourteenth century as a prophylactic against veneral disease. Recent studies have shown it to be a remarkably effective contraceptive. It is today the world's most widely used contraceptive, although the second most widely used method in the United States.

The single most widely used contraceptive in the United States is the female oral contraceptive. It is highly effective, but relatively expensive and causes unacceptable side effects in certain women. Other female contraceptives have well known advantages and disadvantages. Because of these limitations, male contraceptive is an alternative which is attractive to many people.

The mode and proven methods of male contraceptives all involve stopping the production, the passage, or the transport of the sperm. Each of these in turn separate into the permanent and reversible methods.

The vas deferens is a tube running from the epididymis up the scrotum and the inguinal canal behind the bladder where it joins the seminal vesicles, which are both connected to the ejaculatory duct, which in turn joins the urethra. The function of the vas deferens is to carry sperm from the testicle.

The vas deferens is about 2.5 to 3 mm in diameter and contains a central lumen about one tenth of the total diameter. Surrounding the lumen are circular muscle fibers surrounded by longitudinal muscles and nerves. The function of the muscles and nerves is to squeeze the sperm progressively up along the lumen to the outside of the body.

A vasectomy involves surgically severing the vas deferens. Additionally, steps are taken to prevent accidental recanalization. These include fulguration to destroy the mucosal surface and interposing a connective tissue. For these reasons, the propulsive properties of the vas deferens may be permanently damaged by a vasectomy. While recent results of vasovasectomy indicate higher success rates in the return of sperm, the operation must be considered a permanent and irreversible operation since fertility cannot be ensured following reanastomosis of the vas deferens.

Several surgical procedures have been developed for reversible vas deferens occlusion. The first was the insertion of a surgical thread into the lumen of the vas deferens. A surgically implanted intravascular plug is disclosed in U.S. Pat. No. 3,589,355.

The vas deferens may be surgically severed and hollow plastic tubes attached to the two ends. These tubes may then be connected by a solid plug to prevent sperm transport. A hollow plug may be inserted to surgically reverse the procedure. This is disclosed in U.S. Pat. No. 3,990,434.

The vas deferens need not be completely severed, but only surgically slit to insert a cylindrical plug, which is attached through the slit to a hollow cylinder surrounding the vas deferens. The use of this device, discussed in U.S. Pat. No. 4,200,088, is said to cause less damage to the muscles of the vas deferens, increasing the chances the operation may be successfully reversed and fertility restored.

SUMMARY OF THE INVENTION

The present invention is a class of devices and methods of male sterilization which is both reversible and involves only non-surgical procedures. Generally speaking, the present invention involves inserting a plug through the urethra to block the passage of sperm and the consequent fertilization during intercourse.

A first embodiment of the invention envisions a device and method of blocking the passage of sperm by the temporary insertion of the plug into the posterior of the urethra. Such a device may be emplaced and removed by the user.

A second embodiment of the invention involves the placement of a smaller plug into the male reproductive tract at the juncture of the ejaculatory ducts with the urethra or in the vas deferens. Such a device would be medically implanted and medically removed and would be as temporary or as permanent as desired.

The specific devices may utilize a variety of known enlarging plugs which when inserted in place would expand or inflate and when inserted into the urethra or male reproductive tract would prevent sperm from emission or ejaculation.

A first object of the invention is to provide a male contraceptive which is both as effective, and as reversible, as other accepted methods.

A second object of the invention is to provide a male contraceptive which does not affect the immune system or the hormone system by severing the blood testes barrier.

A third object of the invention is to provide a male contraceptive which does not require a first surgical procedure for implantation and a second surgical procedure for reversal.

A fourth object of the invention is to provide a male contraceptive which does not alter the external sensation as a condom can.

A fifth object of the invention is to provide a male contraceptive which can alter the internal sensation to provide a stronger and more prolonged male orgasm.

The invention accordingly comprises the several steps and the relation of one or more of such steps with respect to each of the others, and the apparatus embodying features of construction, combinations of elements and arrangements of parts which are adapted to effect such steps, all as exemplified in the following detailed disclosure, and the scope of the invention will be indicated in the claims.

BRIEF DESCRIPTION OF THE DRAWINGS

The invention will be better understood and the objects other than those set forth above will become apparent when consideration is given to the following detailed description thereof. Such description makes reference to the annexed drawings wherein.

DESCRIPTION OF THE PREFERRED EMBODIMENTS

Figure 1:
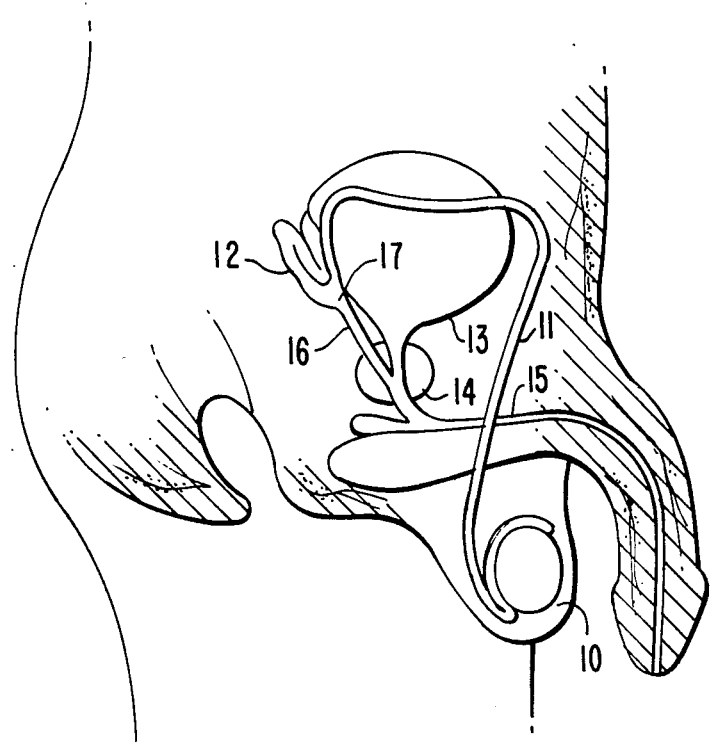
FIG. 1 is a diagrammatic view of the male reproductive and urological systems with which this invention cooperates.

FIG. 1 discloses those portions of the male reproductive system and the urological system with which the present invention cooperates to permit nonsurgical reversible occlusion of sperm passage, thereby achieving male contraception.

Sperm are created in the testes (10) and after transferring the epididymis are propelled up the lumens of the two vas deferens (11) to the seminal vesicles (12) located underneath the bladder (13). The prostate gland (14) secretes the semen which carries the sperm into and through the urethra (15).

Broadly speaking, this invention is a method and device for blocking the passage of the sperm within the vas deferens or within the ejaculatory duct, or within the urethra. The invention involves the nonsurgical insertion of the plug into the urethra and from there to the lumen of the selected organ.

Figure 2:
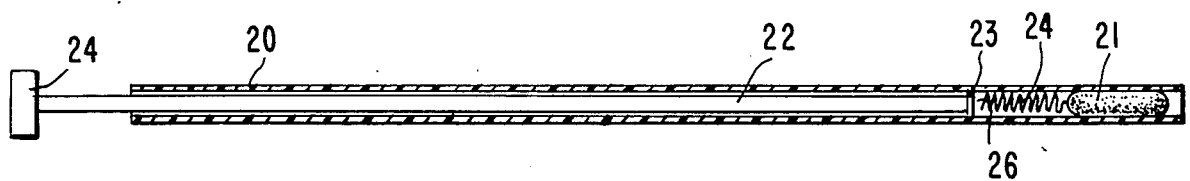
FIG. 2 is an enlarged longitudinal cross sectional view of a first embodiment of the occlusive device of the present invention.

The first embodiment, shown in in FIG. 2, also has an elongated hollow tube (20). The tube (20) will be of a length sufficient to pass through the urethra (15), into the ejaculatory duct (16), past the seminal vesicles (12) and into the opening (17) of first one and then the other of the vas deferens (11). At one end of the tube (20) is a elongated compressive plug (21). Also within the tube (20) is a plunger (22) having a face (23) and handle (24) which extends from the other end of the tube (20). Between the face (23) is a retrieval line (25) attached to the elongated compressive plug and detachably attached to the plunger face (23) by hook (26) or other suitable means. The other end of the tube will extend several inches beyond the urethra to allow the physician to carry out the following procedure. Alternatively, the tube (20) may be shorter and be attached to a known lighted surgical instrument allowing the physician to place the plug visually.

This device is inserted by the physician to ensure that the end of the elongated hollow tube (20) is at the opening (16) of the ejaculatory duct, or other place selected. The plunger is then depressed, pushing the elongated compressive plug out of the tube (20). The tube (20) is then withdrawn and the retrieval line (25) which extends into the urethra is disconnected from the hook (26) on the plunger (22).

The elongated compressive plug (21) may be of rubber, foam or other compressible material so it will simply expand to block the lumen when pushed from the end of the elongated hollow tube (20). Alternatively, the elongated compressive plug (21) may be of a composition which expands under the influence of heat or moisture.

This embodiment may remain in the two vas deferens for an extended period. It may be easily and rapidly removed by a physician in a second nonsurgical procedure which will immediately restore full fertility to the male user.

Figure 3:
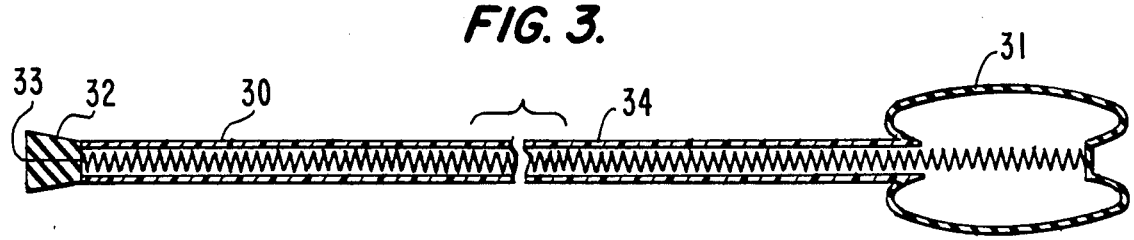
FIG. 3 is an enlarged longitudinal cross sectional view of a second embodiment of the occlusive device of the present invention.

In the embodiment shown in FIG. 3, there is an elongated hollow tube (30) with an outside diameter small enough to fit comfortable within the urethra. Since this will remain within the body for a period of time it must be of a suitably non-physiologically reactive substance, such as polyvinyl chloride or other plastic.

At one end of the elongated hollow tube is an elongated elastic cap (31) of rubber or other suitable composition. The cap (31) is attached to the end of the tube (30) so that when a suitable fluid, which may be liquid or gas, is injected into the tube (30) the cap (31) will expand to a size to completely block the lumen.

At the other end of the elongated hollow tube (30) is a plug (32) sealing the end and thus the interior of the tube (30) in fluid tight manner. The plug (32) has a valve (33) to allow fluid to be inserted or withdrawn. This valve (33) may be a simple aperture which is normally closed by the compressive forces of the plug (32) within the tube (30), or may be closed by spring loading a ball against the apeture. The valve (33) may be opened by pressing it with the hub of a syringe.

Within the elongated hollow tube is a compressible or flexible spring or core (34) which may run from the cap (31) to the plug (32). The function of this flexible spring or core is to ensure that the elongated elastic cap maintains its intended shape and position as it is inserted in the urethra.

The position of the elongated elastic cap when inflated is preferably at the base of the penis, but is not critical and therefore the length of the elongated hollow tube is not critical.

In operation the elongated hollow tube (30) is inserted into the urethra for its full length. A soothing lubricant should be used and a topical anesthetic may also be used. After insertion, the valve (33) is then opened and fluid is injected into the tube (30) to inflate the elongated elastic cap (31). This procedure is then reversed following intercourse and the entire device is removed from the urethra. These simple procedures may be carried out by the user without the assistance of a health care professional.

Both embodiments achieve a fully effective and fully reversible male contraceptive without the severing of the muscle, or nerves, or wall of the vas deferens. Thus, the natural immune system and the natural hormone system are unaffected.

It will thus be seen that the objects set forth above, among those made apparent from the preceding description, are efficiently attained and, since certain changes may be made in carrying out the above method and in the article set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A contraceptive device for achieving reversible male sterilization comprising in combination:
    (a) an elongated hollow tube having an outside diameter allowing it to be inserted into the urethra;
    (b) an expandable elongated elastic cap attached to one end of said elongated hollow tube and forming a fluid tight seal with said elongated hollow tube;
    (c) a plug attached to the other end of said elongated hollow tube forming a fluid tight seal with said elongated hollow tube and said elongated elastic cap;
    (d) a flexible spring within said elongated hollow tube said flexible spring extending within said elongated elastic cap and holding it as an extension of said elongated hollow tube;
    (e) a valve within said plug allowing selective ingress and egress of fluid, and;
    (f) means cooperating with said valve to insert fluid within said tube to expand said elongated elastic cap to occupy the lumen and to prevent the passage of the sperm.

* * * * *